(12) United States Patent
Kraus

(10) Patent No.: US 9,198,777 B2
(45) Date of Patent: Dec. 1, 2015

(54) MANIPULATING TOOL FOR A MEDICAL IMPLANT, MEDICAL IMPLANT AND KIT OF PARTS COMPRISING A MANIPULATING TOOL AND IMPLANT

(76) Inventor: Kilian Kraus, Werneck (DE)

( * ) Notice: Subject to any disclaimer, the term of this patent is extended or adjusted under 35 U.S.C. 154(b) by 1161 days.

(21) Appl. No.: 12/261,234

(22) Filed: Oct. 30, 2008

(65) Prior Publication Data

US 2009/0112220 A1    Apr. 30, 2009

(30) Foreign Application Priority Data

Oct. 30, 2007   (DE) .......................... 10 2007 052 173

(51) Int. Cl.
 *A61B 17/70* (2006.01)
 *A61F 2/46* (2006.01)
 *A61F 2/44* (2006.01)
 *A61F 2/30* (2006.01)

(52) U.S. Cl.
 CPC .................. *A61F 2/4611* (2013.01); *A61F 2/44* (2013.01); *A61F 2/4455* (2013.01); *A61F 2002/3055* (2013.01); *A61F 2002/30337* (2013.01); *A61F 2002/30476* (2013.01); *A61F 2002/30505* (2013.01); *A61F 2002/30523* (2013.01); *A61F 2002/30601* (2013.01); *A61F 2002/4627* (2013.01); *A61F 2220/0025* (2013.01); *A61F 2220/0033* (2013.01)

(58) Field of Classification Search
 CPC ........ A61F 2/44; A61F 2/4455; A61F 2/4611
 USPC ..................... 606/86 A, 99; 623/17.11–17.16
 See application file for complete search history.

(56) References Cited

U.S. PATENT DOCUMENTS

| | | | |
|---|---|---|---|
| 6,319,257 B1 | 11/2001 | Carignan et al. | |
| 6,752,832 B2 * | 6/2004 | Neumann | 623/17.15 |
| 7,235,104 B2 | 6/2007 | Grinberg et al. | |
| 2005/0131408 A1 * | 6/2005 | Sicvol et al. | 606/61 |
| 2006/0241762 A1 | 10/2006 | Kraus | |
| 2007/0032790 A1 * | 2/2007 | Aschmann et al. | 606/61 |
| 2007/0162010 A1 * | 7/2007 | Chao et al. | 606/61 |
| 2007/0213826 A1 | 9/2007 | Smith et al. | |
| 2008/0243254 A1 * | 10/2008 | Butler | 623/17.16 |
| 2008/0319477 A1 * | 12/2008 | Justis et al. | 606/232 |
| 2009/0125032 A1 * | 5/2009 | Gutierrez et al. | 606/99 |
| 2009/0143828 A1 * | 6/2009 | Stad et al. | 606/86 A |

FOREIGN PATENT DOCUMENTS

| | | |
|---|---|---|
| DE | 691 09 768 T2 | 10/1995 |
| DE | 196 04 494 A1 | 8/1997 |

(Continued)

*Primary Examiner* — Edward Moran
(74) *Attorney, Agent, or Firm* — Laurence Greenberg; Werner Stemer; Ralph Locher

(57) ABSTRACT

A manipulating tool for a medical implant includes an actuating rod. The rod has a rear end with a grip part and a fixing element at the front end for the releasable axial fixing of the implant. The implant has a counter element suitable for fixing, which has at least two undercuts spaced apart relative to an axis of its body with one respective holding surface oriented in the direction of the interior of the body. The manipulating tool has at least two clamping jaws being at a radial distance from the central longitudinal axis of the actuating rod, for engaging behind the undercuts on the implant side. The clamping jaws are spaced apart in the peripheral direction. A kit for implant medicine includes a medical implant and a corresponding manipulating tool.

18 Claims, 10 Drawing Sheets

(56) References Cited

FOREIGN PATENT DOCUMENTS

| EP | 0470912 | A2 | 2/1992 |
| EP | 1219266 | A1 | 7/2002 |
| EP | 1818025 | A2 | 8/2007 |
| FR | 2663840 | A1 | 1/1992 |
| WO | 2005/055887 | A2 | 6/2005 |
| WO | 2006055168 | A2 | 5/2006 |

* cited by examiner

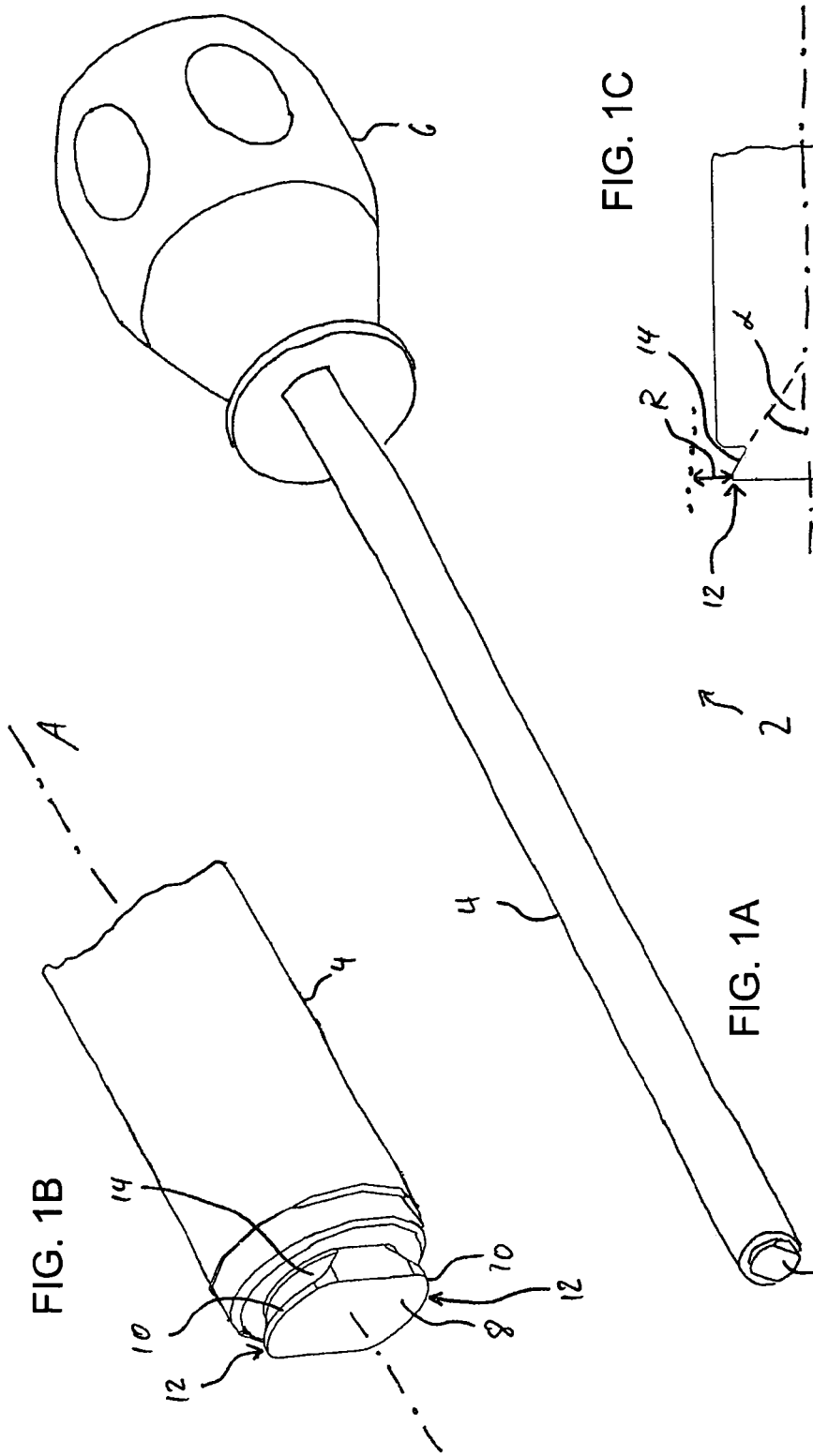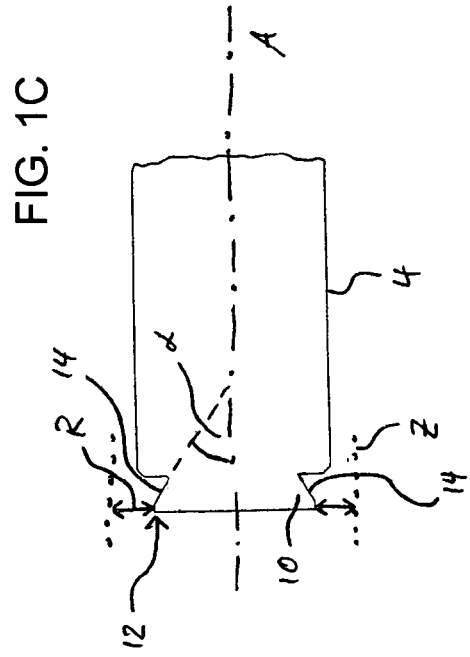

MANIPULATING TOOL FOR A MEDICAL IMPLANT, MEDICAL IMPLANT AND KIT OF PARTS COMPRISING A MANIPULATING TOOL AND IMPLANT

CROSS-REFERENCE TO RELATED APPLICATION

This application claims the priority, under 35 U.S.C. §119, of German patent application DE 10 2007 052 173.3, filed Oct. 30, 2007; the prior application is herewith incorporated by reference in its entirety.

BACKGROUND OF THE INVENTION

Field of the Invention

The invention relates to a manipulating tool for a medical implant, at the rear end thereof a grip part being present and at the front end thereof a fixing element being present for the releasable axial fixing of the implant. Such a manipulating tool is disclosed, for example, in my earlier patent application US 2006/0241762 A1 and its counterpart international PCT publication WO 2005/055887.

The invention further relates to a medical implant. Such implants are widely available as therapeutic measures for replacing a damaged body part. In addition to implants, for example for teeth and joints, such implants also exist for replacing a damaged vertebra. It is important for the success of an operation that the implant is able to be accurately and reliably positioned at its desired location.

Finally, the invention further relates to a kit of parts which comprises a medical implant and a manipulating tool.

European patent EP 0 470 912 and its German counterpart DE 691 09 768 T2 disclose a manipulating tool for a hip joint prosthesis. This is hooked onto undercuts present in the prosthesis by means of cams in the manner of a bayonet closure. For rotationally fixing the manipulating tool to the implant, a plunger is forced into the implant, so that the locking cams engage with a frictional connection in the undercuts on the implant side.

German published patent application DE 196 04 494 A1 discloses a further tool for implanting an endoprosthesis in the cavity of a human bone. The prosthesis is fixed to the manipulating tool in the axial direction by means of a pin. The pin extending in the axial direction has a transverse extension which, when rotating the pin, engages in a suitable undercut of the implant.

As noted above, my earlier specification in US 2006/0241762 A1 and WO 2005/055887 discloses a manipulating tool for a height-adjustable vertebral column implant. The manipulating tool is designed for connecting to the implant such that it may be inserted or screwed with an interference fit into a corresponding opening of the implant. If the manipulating tool is inserted into the implant, a frictional mechanical connection possibly exists between the contact surfaces of the two components. A frictional connection is generally not designed for high loading forces. A screw connection is able to be subjected to considerably greater loads in the axial direction of the manipulating tool, when the tool bears at its front end a radial peripheral thread. However, it is substantially more complicated to separate the screwed implant from the manipulating tool. The possibility for easily separating the implant and the manipulating tool is, in particular, relevant as separating the implant and the manipulating tool causes a possible source of error during operations and an unnecessary loss of time.

SUMMARY OF THE INVENTION

It is accordingly an object of the invention to provide a manipulating tool, a medical implant, and a kit of parts, which overcome the above-mentioned disadvantages of the heretofore-known devices and methods of this general type and which render possible a reliable non-positive connection between the implant and the manipulating tool and which allows an easy release.

With the foregoing and other objects in view there is provided, in accordance with the invention, a manipulating tool for a medical implant, comprising:

an actuating rod defining a central longitudinal axis and having a front end and a rear end;

a grip part at the rear end of the actuating rod;

a fixing element at the front end of the actuating rod, for releasably axially fixing the implant, the fixing element having at least two clamping jaws spacing at a radial distance from the central longitudinal axis of the actuating rod and, relative to an imaginary cylinder surface extending coaxially with the central longitudinal axis, mutually spaced apart in a peripheral direction, for respectively engaging behind at least one counter element on the implant; and a locking device for rotationally locking the manipulating tool to the implant, the locking device including at least one locking element held in rotationally fixed connection with the actuating rod and held axially displaceably on the actuating rod between a front position, defining an operating position thereof, and a rear position, defining a position of repose thereof.

According to the invention, the manipulating tool for a medical implant comprises an actuating rod, at the rear end thereof a grip part being present and at the front end thereof a fixing element being present for the releasable axial fixing of the implant. The fixing element has at least two clamping jaws which maintain a radial distance from the central longitudinal axis of the actuating rod. Relative to an imaginary cylinder surface extending coaxially to the central longitudinal axis of the actuating rod, the clamping jaws are mutually spaced apart in the peripheral direction. The clamping jaws of the manipulating tool are used for engaging behind at least one counter element on the implant side. A device for rotationally locking the manipulating tool to an implant comprises at least one locking element which is connected fixedly in terms of rotation to the actuating rod. The locking element is held axially displaceably on the actuating rod between a front position, its operating position, and a rear position, its resting position.

The following observation underlies the inventive measures: by engaging behind at least one counter element on the implant side a simple axial fixing of the implant may be achieved. As the at least two clamping jaws are spaced apart in the peripheral direction, a locking between the manipulating tool and the implant is possible with less than one complete rotation. The implant and the manipulating tool may thus be connected to one another and separated from one another rapidly and easily. The implant and the manipulating tool may, for example, be connected to one another fixedly in terms of rotation by a frictional connection between the clamping jaws and a counter element on the implant side. The possibility for rotationally locking the implant relative to the manipulating tool extends the operative range thereof. Such a manipulating tool allows a reliable, accurate positioning of the implant, and a positioning process of the implant being possible from now on in which the implant is additionally rotated about the central longitudinal axis of the manipulating tool. The locking element is configured such that the locking element is axially displaceable between a front position, its operating position, and a rear position, its resting position and is held on the actuating rod. Such an embodiment of the locking element offers the possibility, when producing the axial fixing, of removing the locking element from the region of the fixing element for rotational fixing, so that the axial fixing may be produced unhindered.

According to a first embodiment, the locking element is spring-loaded in the direction of its operating position. The operation of the manipulating tool is from now on improved by the locking element being spring-loaded and being able to be engaged in its operating position. Moreover, with a locking element pretensioned in such a manner in the direction of its locked position, the latching of the rotational locking is not able to be overlooked.

According to an embodiment, the device for the rotational locking comprises a hollow tube enclosing the actuating rod and axially displaceable thereon. The front end of the hollow tube bears at least one locking element fixedly connected thereto. Rotational locking in the form of a hollow tube is particularly stable and, moreover, protects the surrounding tissue from injuries from the actuating rod.

According to a development, the hollow tube is pretensioned by a spring element being supported with its rear end on the actuating rod and with its front end on the hollow tube. The hollow tube is thus pretensioned by the spring element relative to the actuating rod. This naturally also applies to the locking element connected to the hollow tube. The operation of the manipulating tool is improved by the locking element present on the hollow tube being pressed by the spring force of the spring element into its corresponding abutment on the implant side.

According to a further embodiment, the rear end of the hollow tube is radially widened, forming a housing. The at least one spring element is arranged in this housing. The hollow tube on the housing may be particularly easily retracted, which simplifies the operation of the manipulating tool.

The hollow tube is, according to a development, held in a manner which is secure against loss on the actuating rod. Should the hollow tube during an operation inadvertently fall to the floor, for hygiene reasons, it is necessary to disinfect the hollow tube again. The disinfection process leads to an interruption of the operation. Thus it is particularly advantageous if the hollow tube is held on the actuating rod in a manner which is secure against loss.

The securing against loss is, according to one embodiment, formed by a latching element being present spring-loaded substantially in the radial direction, engaging in a peripheral groove with axial clearance, the axial clearance corresponding to the movement path between the operating and resting positions. A manipulating tool according to the above embodiment has an actuating rod and a hollow tube which may be releasably fixed to one another. The hollow tube has, relative to the actuating rod, a movement path defined by the axial clearance of the peripheral groove. At the same time, the peripheral groove serves for securing the hollow tube against loss relative to the actuating rod and thus fulfils particularly advantageously a dual function.

The securing against loss of the hollow tube relative to the actuating rod may, according to one embodiment, be improved by at least one protruding annular projection being located on the outer periphery of the actuating rod, between the front end and the peripheral groove. Should the hollow tube be released from the peripheral groove with axial clearance, the hollow tube is additionally secured by the peripheral annular projection.

For the connection between the hollow tube and the actuating rod which is fixed in terms of rotation, the manipulating tool has a rotational fixing according to a further embodiment. The rotational fixing consists of a flattened portion and a projection, the flattened portion on the actuating rod extending axially at least over the front partial region and reaching into the front face. A projection is present on the inner face of the hollow tube, which bears with a flat side against the flattened portion. The non-positive connection of such a rotationally fixed connection between the hollow tube and the actuating rod is produced in the front region of the manipulating tool. This results in the advantage that when inserting the actuating rod into the hollow tube, the precision fit which leads to the rotationally fixed connection, i.e. the fit between the flat side of the projection and the flattened portion, does not initially have to be produced. Initially only the actuating rod has to be inserted into the hollow tube. The positive connection resulting in the connection between a flat side of the hollow tube and a flattened portion of the actuating rod, which is fixed in terms of rotation, is only produced when the actuating rod is already held in the hollow tube in a manner which is secure against loss. The operational reliability of the manipulating tool may be significantly improved.

The flattened portion which extends over a partial region of the actuating rod is, according to a development, formed from the base of an axial groove. The projection extending into this axial groove is of complementary configuration. The projection positively engaging in the axial groove, in particular the wall parts thereof oriented perpendicularly to the base of the axial groove, form clearly defined bearing surfaces with the side walls of the axial groove, also preferably oriented perpendicular to the base. Advantageously, in this manner a connection which is reliable, which may be subjected to high mechanical loads and which is fixed in terms of rotation may be achieved between the hollow tube and the actuating rod.

According to one embodiment, the projection projects beyond the front face of the hollow tube and forms at least one locking element. Advantageously, this at least one projection fulfils a dual function. The projection acts both as a locking element for rotationally fixing the implant relative to the manipulating tool and also as part of the rotational fixing between the hollow tube and the actuating rod.

According to one embodiment, the outer edges of the clamping jaws facing away from the central longitudinal axis are designed such that the clamping jaws are respectively at the same radial distance from a circle circumscribing the clamping jaws. The outer edges of the clamping jaws arranged at a uniform distance from a circumscribed circle serve to reduce the radial clearance between the fixing element of the manipulating tool and the bearing surfaces of the counter element on the implant side. The common radial distance being constant irrespective of said locking element being in the operating position or the position of response.

The radial positive connection between the clamping jaws and the bearing surfaces of the counter element may be improved by the outer edges of the clamping jaws being developed as segments of a common circular arc. The mechanical connection between the implant and the manipulating tool is further improved by the sides of the clamping jaws oriented toward the rear end of the manipulating tool, which cooperate with corresponding surfaces of the counter element, having an incline relative to the central longitudinal axis of the actuating rod. According to such an embodiment, the sides of the clamping jaws oriented to the rear enclose with the central longitudinal axis of the actuating rod an acute angle opening toward the front end of the manipulating tool. Such inclined surfaces of the clamping jaws effect a centering of the fixing element in the counter element on the implant side about the central longitudinal axis of the actuating rod.

The aforementioned surfaces of the fixing element are, according to a further embodiment, partial surfaces of a conical surface tapering toward the rear end of the manipulating tool. The clamping jaws designed in this manner bear over a large surface area against the corresponding counter surface on the implant side and, therefore, allow a reception of the implant by the manipulating tool with a small amount of surface pressure.

The actuating rod, including the grip part, is, according to a further embodiment, penetrated by a central bore, which is used for receiving a drive shaft. The drive shaft has at its front end a drive pinion and at its rear end a rotary knob. By guiding the drive shaft in the inside of the actuating rod, the risk of injury for the surrounding tissue when actuating the drive shaft may be minimized.

According to a further embodiment, the drive shaft is axially displaceable between a neutral position and an engagement position. In the neutral position, the front face of the drive pinion is located axially to the rear and in the engagement position axially in front of the front face of the actuating rod. If the drive shaft is located in the engagement position, for example, the height of an implant may be altered. In order to ensure that during the alteration of the position of the implant the height thereof remains unaltered, the drive shaft may be moved from the engagement position into the neutral position. The operation of the manipulating tool may be markedly improved in this manner.

According to a development, the grip part at its rear end has a radial peripheral groove. A spring-loaded latching element present in the rotary grip engages in this groove with a positive connection which is effective in the axial direction. Particularly advantageously, the groove fulfils a dual function. It acts together with the latching element firstly as security against loss and secondly, by the positive connection which is effective in the axial direction between the latching element and groove, defines the neutral position of the drive shaft.

The engagement position of the drive shaft is defined by a bearing surface present on the grip part, cooperating with the rotary knob. Advantageously, when releasing the drive shaft from the engagement position no latching has to be overcome, as the engagement position is mechanically defined by means of a bearing surface. The drive shaft is thus able to be easily pulled back from the engagement position into the neutral position.

The implant according to the invention comprises a body and a counter element present thereon for releasably fixing a manipulating tool. The counter element has at least two undercuts spaced apart relative to an axis of the body, with one respective holding surface oriented in the direction of the interior of the body. The counter element, moreover, for rotationally fixing the implant relative to a manipulating tool, has a bearing surface not oriented coaxially to the axis. The implant according to the invention allows a particularly simple latching to a manipulating tool by a positive undercut on the holding surfaces oriented in the direction of the interior of the body. A rotational fixing between a manipulating tool and a surface oriented coaxially to the axis of the implant is—provided the manipulating tool is connected thereto along the axis of the implant—only possible by a frictional connection. The rotational fixing between the implant and the manipulating tool is thus limited to the maximum frictional force of the frictional connection. A rotational fixing by means of a bearing surface, not oriented coaxially to the axis of the implant, allows an improved non-positive connection for the rotational fixing of the implant.

With the above and other objects in view there is also provided, in accordance with the invention, an implant, comprising:

a body defining an axis and having an interior;

a counter element disposed on the body for releasably fixing a manipulating tool thereto, the counter element having at least two undercuts spaced apart relative to the axis of the body and each having a respective holding surface oriented towards the interior of the body; and a bearing surface on the counter element for rotationally fixing the implant relative to the manipulating tool, the bearing surface being oriented non-coaxially with the axis of the body.

According to a first embodiment of the implant, the bearing surface comprises a surface extending parallel to the axis. If the bearing surface is oriented parallel to the axis of the implant, the insertion of the manipulating tool along the axis of the implant is substantially simplified.

According to a further embodiment, the implant has such holding surfaces which are respectively formed by the wall of a recess incorporated in the body. By the integration of the holding surfaces into the wall, the surface of the implant may be maintained substantially smooth, which reduces the risk of injury when the implant is being inserted.

According to a further embodiment, the holding surfaces enclose with the axis of the body an acute angle opening toward the interior of the body. Such holding surfaces which are inclined relative to the axis of the body effect an axial centering of the implant relative to its axis. Such a measure allows a reception of the implant, without clearance, by a manipulating tool.

For the further improvement of the reception of the implant by a manipulating tool, the holding surfaces are developed as partial surfaces of a conical surface widening toward its interior. By such a design of the holding surfaces, the holding surfaces bear over a large surface area against the corresponding counter surfaces of a manipulating tool, which leads to a small surface pressure on the holding surfaces and allows a secure reception of the implant by a manipulating tool.

The implant according to the invention may, according to one embodiment, be a height-adjustable implant. The implant is characterized by the following features: the body of the implant is formed by a first and a second component, which are axially movable relative to one another and held fixedly in terms of rotation against one another along a central longitudinal axis of an implant. The components respectively comprise at least two wall segments fixed to a base, which extend in the direction of the central longitudinal axis and are respectively at a radial distance therefrom. Two respective wall segments adjacent in the peripheral direction flank an intermediate space into which a wall segment of the respective other component extends and is axially guided therein. A drive element is arranged in the interior enclosed by the wall segments, which cooperates with the second component in the manner of a screw mechanism. The drive element has a toothed wheel arranged coaxially to the central longitudinal axis, which is used for the rotational actuation of the drive element. The drive element is supported in the loading direction on the first component. At least one wall segment of the first component has an access opening penetrating the wall segment, via which the toothed wheel is accessible for the rotational actuation of the drive element by means of a manipulating tool.

An implant according to the aforementioned embodiment is height-adjustable by the drive element present in its interior. The height adjustment takes place by a drive element which is driven by means of a manipulating tool. As a result, it is possible both to receive the implant with a manipulating tool in a secure and mechanically reliable manner, and to adjust the implant in its height. The manipulation of the implant takes place, therefore, merely by means of a single manipulating tool as regards both the adjustment of the height and also its positioning. The handling of the implant may be substantially simplified in this manner.

With the above and other objects in view, there is provided a kit that is particularly suitable in the field of implant medicine. The kit includes the above-summarized implant in the form of a medical implant and a manipulating tool as outline above and specifically configured for manipulating the implant.

Other features which are considered as characteristic for the invention are set forth in the appended claims.

Although the invention is illustrated and described herein as embodied in a manipulating tool, a medical implant, and a corresponding kit, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

BRIEF DESCRIPTION OF THE SEVERAL VIEWS OF THE DRAWING

FIG. 1a to c show a manipulating tool and detailed views of the front end thereof in perspective view and in cross section.

DETAILED DESCRIPTION OF THE INVENTION

Figure 2:
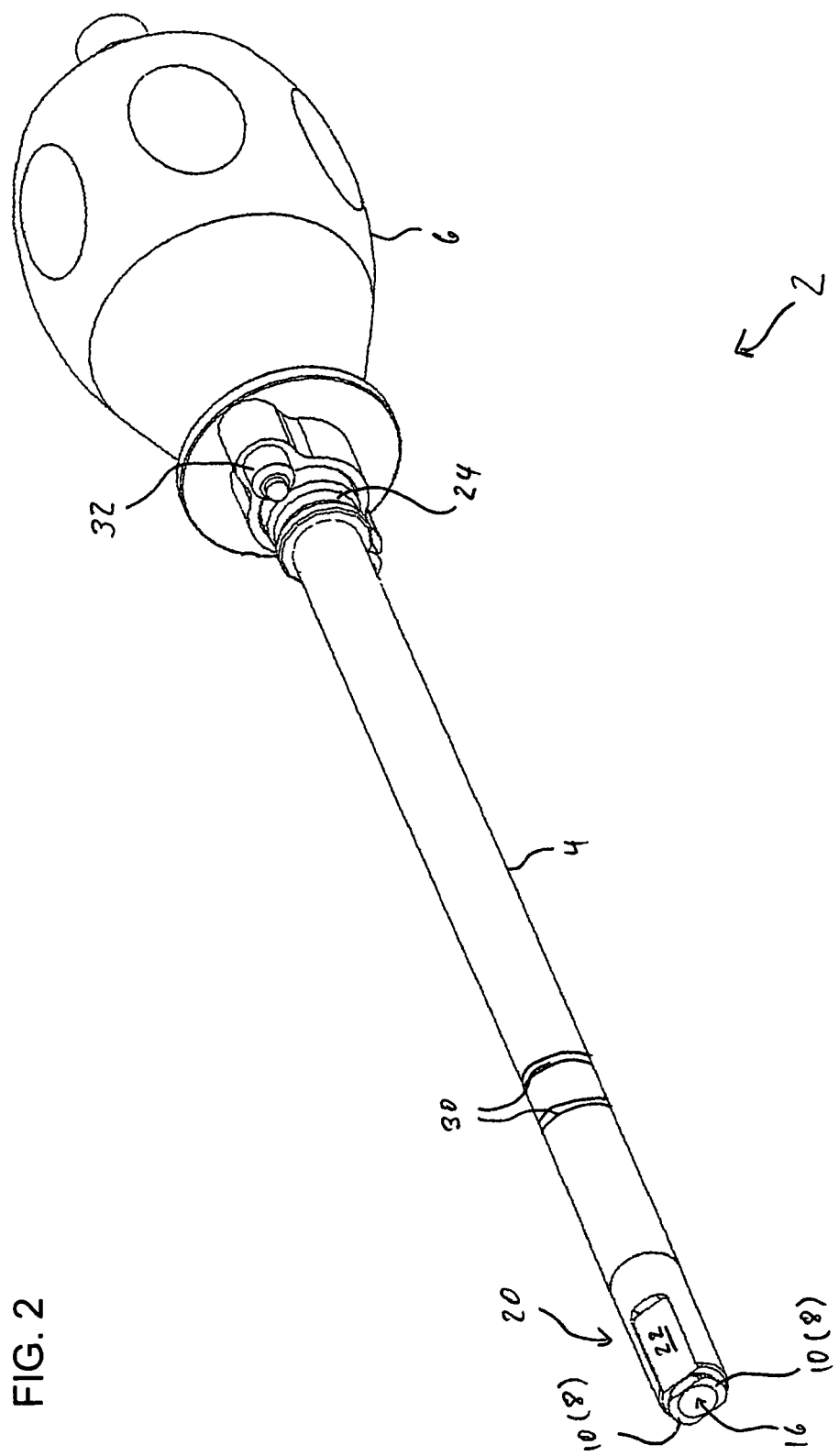
FIGS. 2 and 4 show a manipulating tool in perspective view.

Referring now to the figures of the drawing in detail and first, particularly, to FIG. 1a thereof, the apparatus according to the invention includes a manipulating tool 2 comprising an actuating rod 4. On the rear end of the actuating rod 4 there is provided a grip part 6 and at the front end thereof there is disposed a fixing element 8. The manipulating tool 2 is used for inserting a medical implant. The fixing element 8 has, as the detailed view of the front end of the actuating rod 4 in FIG. 1b shows, two clamping jaws 10, which serve for engaging behind corresponding counter elements on the implant side. The clamping jaws 10 are spaced apart in the radial direction, relative to an imaginary cylinder, which extends coaxially to the central longitudinal axis A of the manipulating tool 2. According to the embodiment shown in FIG. 1b, the clamping jaws 10 of the fixing element 8 are arranged diametrically opposite one another relative to the central longitudinal axis A. The outer edges 12 of the clamping jaws 10 describe segments of a common circular arc. In particular, the outer edges 12 of the clamping jaws 10 describe segments of a circular arc drawn about the central longitudinal axis A. FIG. 1c shows a cross section through the front end of the actuating rod 4. The outer edges 12 of the clamping jaws 10 have a common spacing R relative to an imaginary cylinder Z which extends about the central longitudinal axis A.

The clamping jaws 10 of the manipulating tool 2 may be bodies formed in a different manner, deviating from the views in FIGS. 1a to c. For example, the clamping jaws 10 may be formed by bars or cuboids facing away from the central longitudinal axis A. Moreover, it is not required that the outer edges 12 of the clamping jaws 10, as shown in FIG. 1b, follow a common circular arc about the central longitudinal axis A. For example, clamping jaws 10 may be used which, as outer edges 12, have parallel edges opposing one another relative to the central longitudinal axis A.

The manipulating tool 2 shown in FIGS. 1a to c, serves for receiving a medical implant. For locking the manipulating tool 2 to the medical implant, the clamping jaws 10 at the front end of the actuating rod 4, as FIGS. 1b an 1c show, have surfaces 14 which cooperate with the corresponding counter surfaces on the implant side. In FIG. 1c the direction of one of the surfaces 14 is shown in dotted lines extending as far as the region of the central longitudinal axis A. The surface 14 is oriented such that said surface encloses with the central longitudinal axis A an acute angle α opening toward the front face of the manipulating tool 2. The clamping jaws 10 may be designed deviating from the view in FIGS. 1a to 1c such that said clamping jaws merely have partial surfaces, which are oriented such that they enclose with the central longitudinal axis A an acute angle α.

The surfaces 14 shown in FIGS. 1b and 1c are designed such that they are part of a conical surface tapering toward the rear end of the manipulating tool 2. As is clear from FIG. 1b, the surfaces 14 of the clamping jaws 10 are located on a common conical surface, the cone point thereof being located on the central longitudinal axis A. The cone surface extends symmetrically around the central longitudinal axis A.

FIG. 2 shows a further embodiment for a manipulating tool 2, said manipulating tool comprising at its front end a fixing element 8 with clamping jaws 10. The manipulating tool 2 is penetrated in the longitudinal direction along the central longitudinal axis A, which is not shown in FIG. 2 for reasons of clarity, by a central bore 16. The bore 16 serves for receiving a drive shaft 18, which is intended to be described in connection with FIGS. 3a to c. The clamping jaws 10 of the manipulating tool 2 shown in FIG. 2 are designed as already described in connection with FIGS. 1a to c.

The actuating rod 4 has at its front end an axial groove 20 which extends into the front face of the actuating rod 4. The axial groove 20 is incorporated in the wall of the actuating rod 4. Its base is in the shape of a flattened portion 22, and the wall surfaces adjacent thereto extend perpendicular to the base of the axial groove 20. Viewed in cross section, the axial groove 20 is therefore U-shaped. The axial groove 20 is part of a device for rotationally locking the medical implant on the manipulating tool 2, about which more detail is to be provided in connection with FIGS. 3a to c.

The actuating rod 4 of the manipulating tool 2 has at its rear end a peripheral groove 24 for engaging a spring-loaded latching element. The radial peripheral groove 24 serves for securing a hollow tube 28 against loss, into which the actuating rod 4 may be inserted. The securing against loss between the hollow tube 28 shown in FIG. 3b and the actuating rod 4 is described in more detail in connection with FIGS. 6 and 7. The annular projections 30 present between the front end of the actuating rod 4 and the peripheral groove 24 also serve for securing the hollow tube 28 against loss. The actuating rod 4 is made up of two halves made individually which, preferably, are connected to one another by laser welding. The resulting welded seam forms the annular projections 30.

In the region of the grip part 6 spring elements 32 are located on the actuating rod 4, of which only one is visible in the perspective view selected in FIG. 2. The spring elements 32 serve for the mechanical pretensioning of the hollow tube 28 relative to the actuating rod 4, about which more details are to be provided in connection with FIGS. 6a and b.

Figure 3:
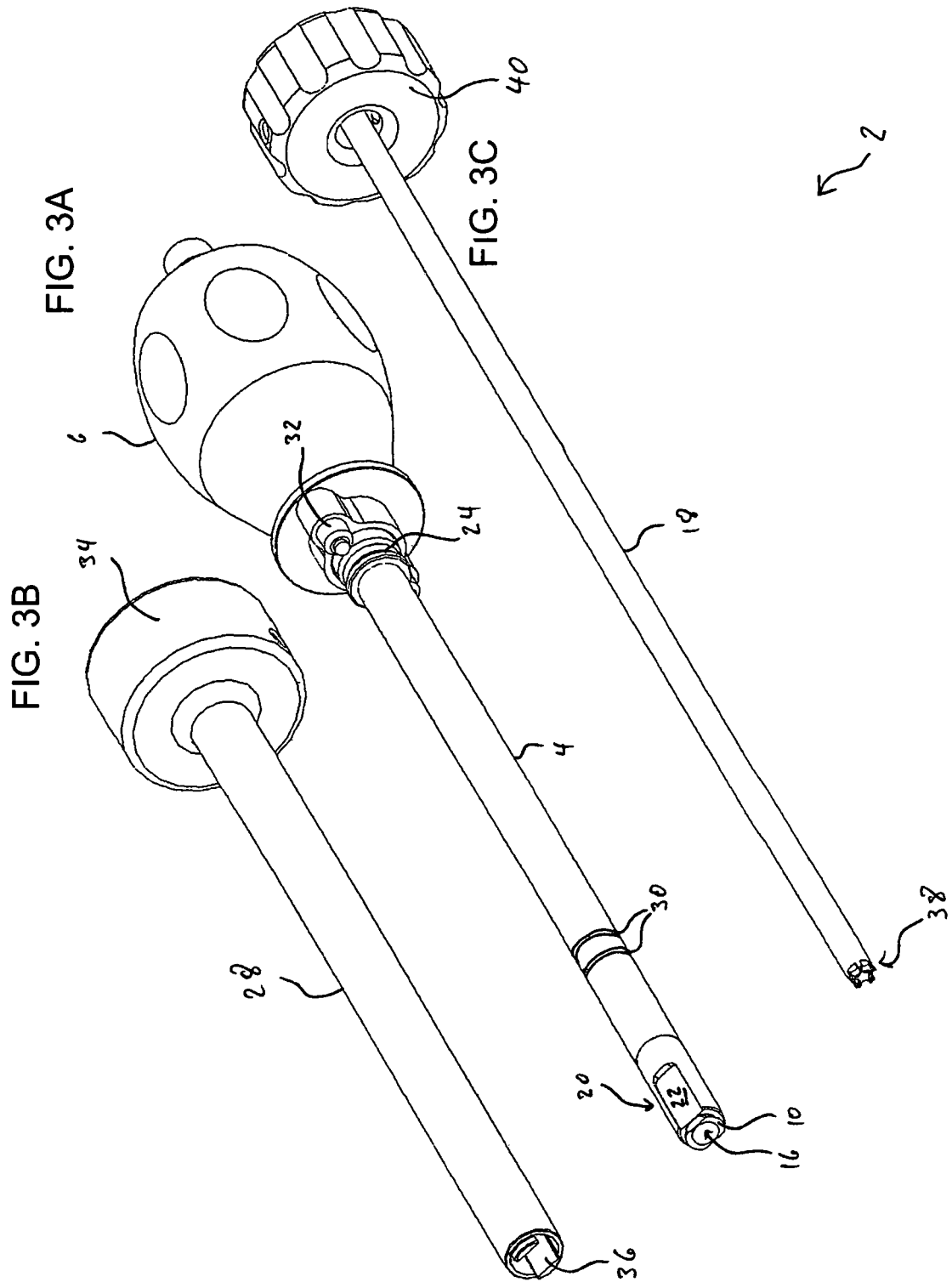
FIG. 3a to c show an actuating rod, a hollow tube and a drive shaft for a manipulating tool in perspective view.

A manipulating tool 2 for receiving a medical implant fulfils a plurality of tasks. Firstly, it is used for the holding of a medical implant in a mechanically reliable and easily releasable manner. The implant is in this connection fixed in the axial direction of the manipulating tool 2 by the jaws 10. FIG. 3a shows the part of the manipulating tool 2 already known from FIG. 2, which substantially comprises the actuating rod 4 and the components connected thereto. The manipulating tool 2, however, not only serves for the axial fixing but also permits a connection of the implant to the manipulating tool 2 which is fixed in terms of rotation.

FIG. 3b shows the already discussed hollow tube 28 into which the actuating rod 4 may be inserted. The hollow tube 28 is at its rear end widened to form a housing 34. At its front end the hollow tube 28 has two projections 36 opposing one another which project from the front face of the hollow tube 28, and a locking element for the reception of a medical implant which is fixed in terms of rotation. The inner faces of the projections 36 form plane-parallel surfaces relative to the central longitudinal axis A of the hollow tube 28, not shown for reasons of clarity. The projections 36 extend on the inner face of the hollow tube 28 in the front region thereof. The projections 36 are configured to fit accurately in axial grooves 20 present at the front end of the actuating rod 4. For rotationally fixing the hollow tube 28 relative to the actuating rod 4 the projections 36 engage in the axial grooves 20 of the actuating rod 4, the internal flat sides of the projections 36 bearing against the flattened portions 22 of the axial grooves 20. The rotational fixing of the hollow tube 28 relative to the actuating rod 4 is, moreover, achieved by the axial groove 20 comprising bearing surfaces, not shown in more detail in FIG. 3a, and oriented substantially perpendicular to the flattened portion 22, which cooperate with the corresponding counter surfaces of the projections 36. The bearing surfaces are the wall surfaces (see FIG. 2) oriented perpendicular to the base of the flattened portion 22.

The axial grooves 20 of the actuating rod 4, as well as the projections 36 of the hollow tube 28, extend in the front regions of the respective components. This simplifies the insertion of the actuating rod 4 in the hollow tube 28. Thus the actuating rod 4 is inserted into the hollow tube 28 from the rear end i.e. in the region of the housing 34, the hollow tube 28 and the actuating rod 4 at this time not yet having to be oriented in the correct direction of rotation relative to one another. Only when the actuating rod 4 is further inserted into the hollow tube 28, do the two components have to be oriented in the correct direction of rotation relative to one another, for engagement of the projections 36 into the axial grooves 20. The hollow tube 28 is from now on connected fixedly in terms of rotation to the actuating rod 4, in particular however also to the grip part 6. The projections 36 also serve for engaging in corresponding counter elements on the implant side, so that in this manner a medical implant may be connected to the manipulating tool 2 fixedly in terms of rotation.

The medical implant may have further internal mechanical functions, for example the implant may be height adjustable. In order, for example, to be able to drive a gear mechanism present in the implant, the actuating rod 4 shown in FIG. 3a has a central bore 16 in which a drive shaft 18 which is shown in FIG. 3c, may be guided. The drive shaft 18 has at its front end a drive pinion 38. At its rear end a rotary knob 40 is connected to the drive shaft 18. The drive shaft 18 is inserted into the central bore 16 of the actuating rod 4, its length being selected such that the drive pinion 38 in the assembled state emerges from the front face of the actuating rod 4. This position is suitable for actuating a drive element present inside the implant. For this reason, this position of the drive shaft 18 and/or of the drive pinion 38 is to be denoted as an engagement position. The drive shaft 18 is, moreover, able to be withdrawn into a neutral position in which the drive pinion 38 does not cooperate with a possibly present drive element of the medical implant received. In the neutral position, the drive pinion moves axially behind the front face of the actuating rod 4. With regard to further embodiments, reference is made to FIG. 7.

Figure 4:
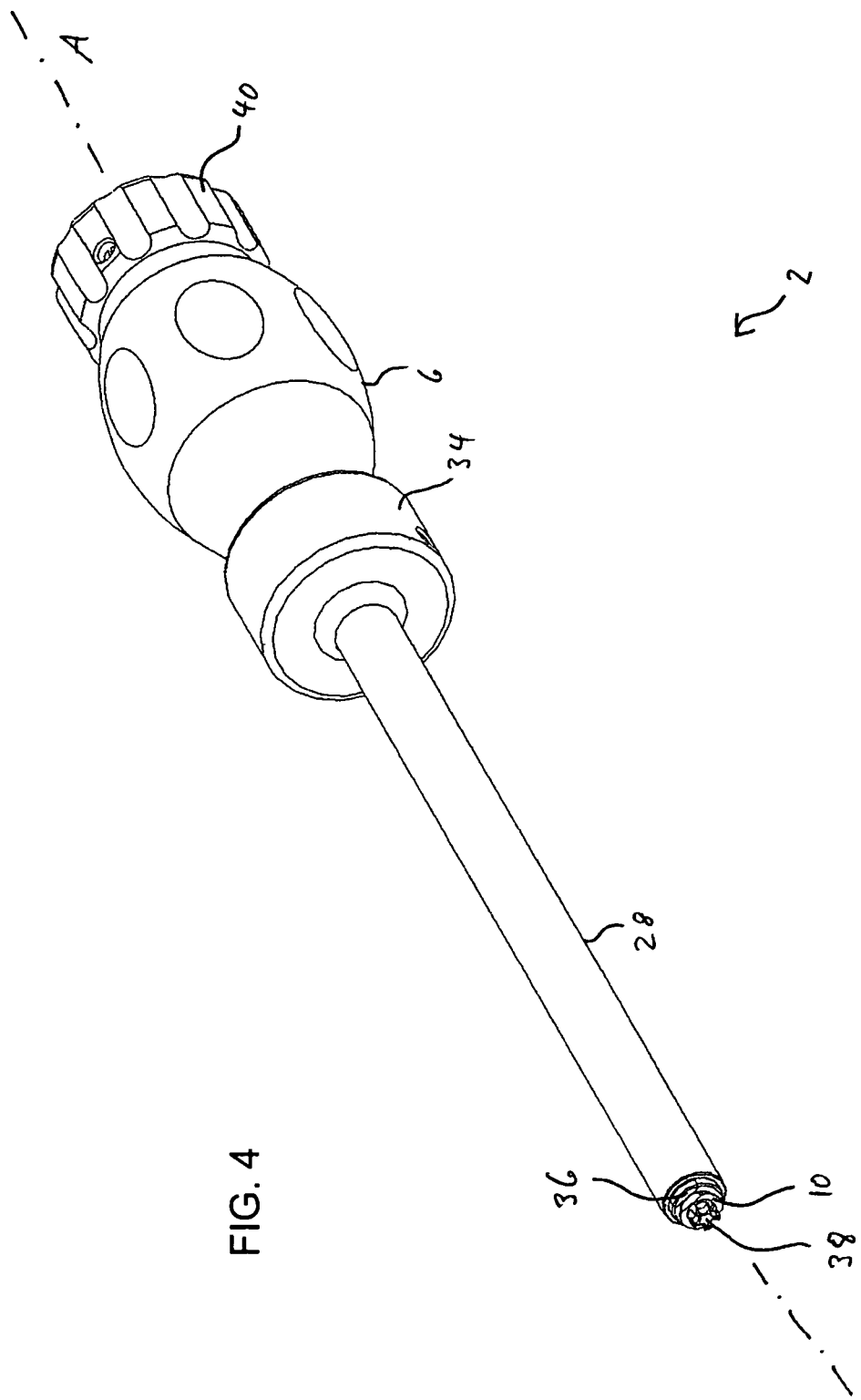

FIG. 4 illustrates a manipulating tool 2 made up of the individual parts shown in FIGS. 3a to 3c. The clamping jaws 10 at the front end of the manipulating tool 2 are spaced apart from one another in the peripheral direction. The projections 36 come to bear in the intermediate spaces. The drive shaft 18 extends along the central longitudinal axis A which at its front end is configured to form a drive pinion 38, and which viewed axially emerges from the front face of the clamping jaws 10. The projections 36 which serve for the reception of a medical implant which is fixed in terms of rotation, are preferably integrally configured with the hollow tube 28 which encloses the actuating rod 4 and the drive shaft 18. The entire hollow tube 28 is displaceable in the axial direction. To this end, the hollow tube 28 on the housing 34 may be retracted. By the position of the grip part 6 and the housing 34, a single-handed operation is possible. The rotary knob 40 present at the rear end of the manipulating tool 2 serves for the rotational actuation of the drive pinion 38.

Figure 5A:
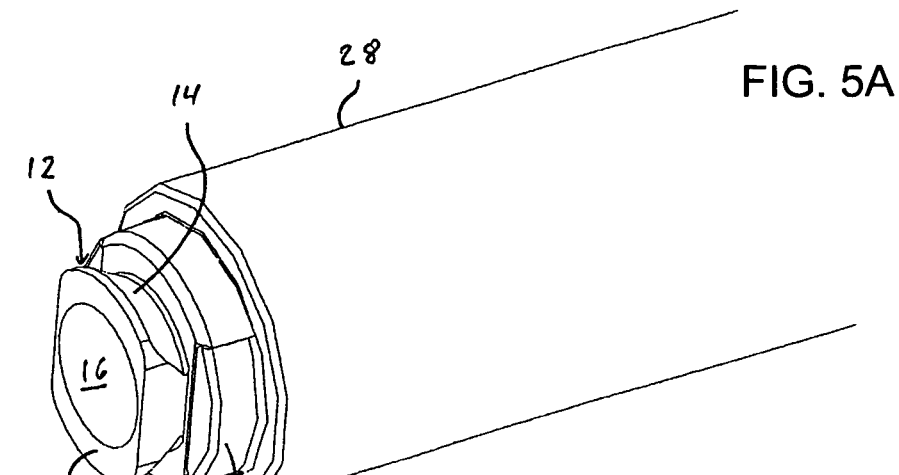
FIG. 5a to c show perspective detailed views of the front end of a manipulating tool.
Figure 5B:
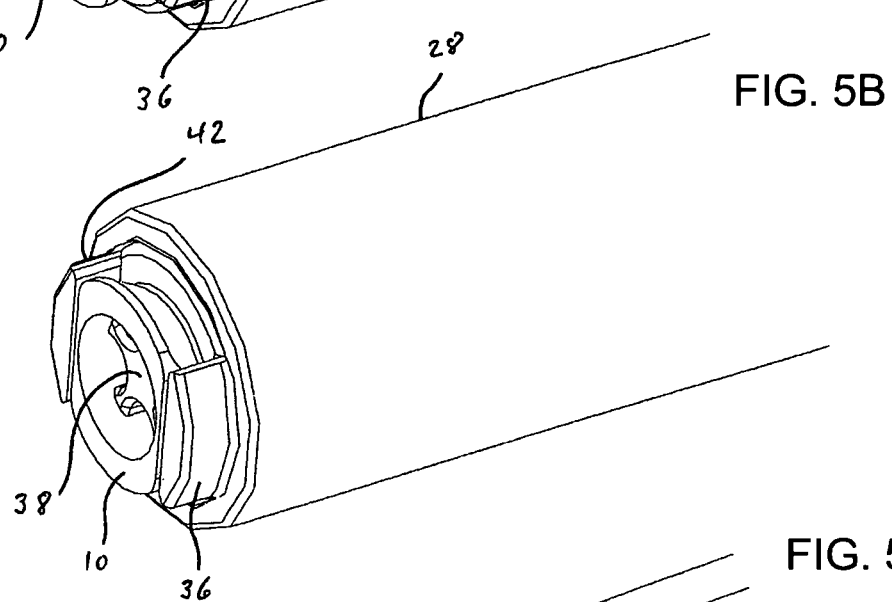
Figure 5C:
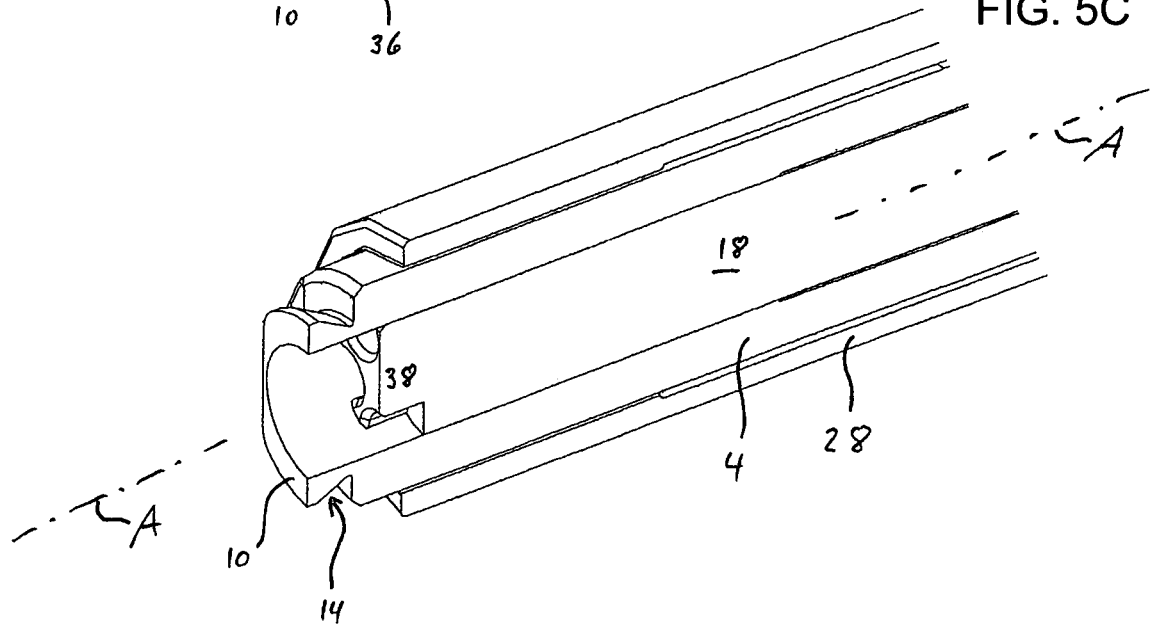

FIGS. 5a to 5c show respectively the front end of the manipulating tool 2. In this case merely the external front end of the hollow tube 28 is visible. The locking of a medical implant to the manipulating tool 2, in the axial direction of the manipulating tool, takes place via the surfaces 14, which interact with the corresponding counter surfaces on the implant side.

FIG. 5a shows the position of the manipulating tool 2 in which, by a 90° rotation about the central longitudinal axis A, the manipulating tool 2 may be locked to an implant. The projections 36 connected to the hollow tube 28 are retracted to such an extent that the surfaces 14 of the clamping jaws 10 facing the rear end of the manipulating tool 2 may engage unhindered during a rotation about the central longitudinal axis A in correspondingly formed undercuts of an implant. For receiving the implant without clearance, in this case preferably the circular segment-shaped outer edges 12 of the clamping jaws 10 slide in correspondingly formed recesses of the implant.

FIG. 5c shows the front part of the manipulating tool 2 shown in FIG. 5a in a sectional perspective view. The drive shaft 18 including the drive pinion 38 is retracted to such an extent into the inside of the actuating rod 4, that an unhindered latching of the clamping jaws 10 to an implant may take place.

FIG. 5b shows the front part of the manipulating tool 2, the projections 36 connected to the hollow tube 28 being axially pushed forward for the connection of the manipulating tool 2 to a medical implant which is fixed in terms of rotation. The front faces of the clamping jaws 10 and the projections 36 are now located in a common plane. The connection between the implant and the manipulating tool 2 which is fixed in terms of rotation, is in principle achieved by the fixing surfaces 42 oriented perpendicular to the front face of the clamping jaws 10, which respectively extend on the axially oriented side edges of the projections 36.

Figure 6A:
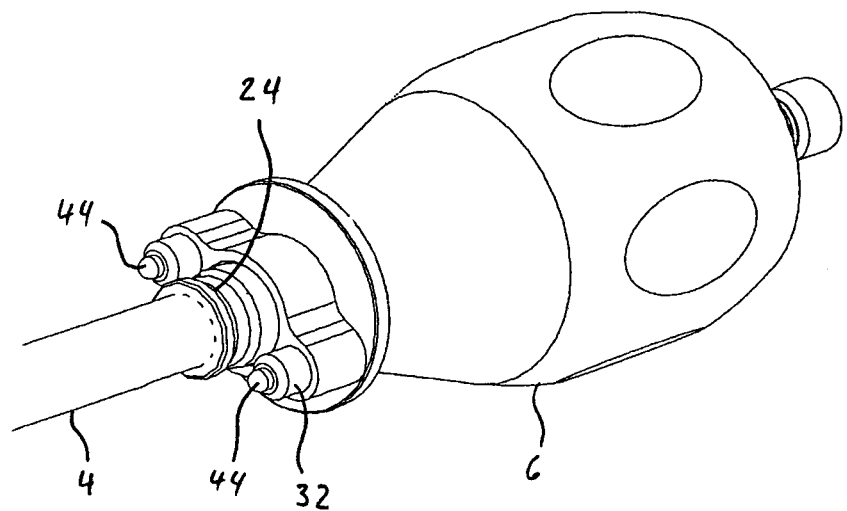
FIG. 6a to b show details of a manipulating tool in the region of the connection between the actuating rod and the hollow tube in perspective view.
Figure 6B:
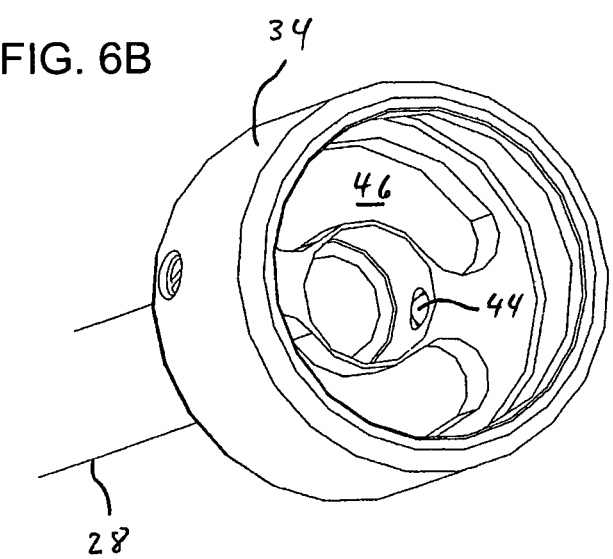

The rear end of the actuating rod 4 is shown in FIG. 6a, and FIG. 6b shows that of the hollow tube 28. The hollow tube 28 is at its rear end widened to form the housing 34. Inside the housing 34 are located recesses 46 in which the spring elements 32 present at the rear end of the actuating rod 4 engage. The spring elements 32 are in this case configured in the manner of ball thrust pieces. A ball 44 present at the front end of the spring elements 32, bears against the base of the recess 46 when the hollow tube 28 is completely pushed onto the actuating rod 4. The spring element 32 is thus supported with its rear end on the actuating rod 4 and with its front end on the hollow tube 28 and/or the housing 34.

A radial peripheral groove 24 is located at the rear end of the actuating rod 4. In the interior of the housing 34 are located the spring-loaded balls 44 of two ball thrust pieces, of which only one is visible. Said balls engage as latching elements with axial clearance in the radial peripheral groove 24. The hollow tube 28 is releasably connected by this non-positive connection in the axial direction to the actuating rod 4. At the same time, the cooperation between the ball thrust pieces present in the housing 34 and the axial peripheral groove 24 secures the hollow tube 28 against loss relative to the actuating rod 4. As already mentioned in connection with FIGS. 2 and 3a, the actuating rod 4 has annular projections 30 between its front end and the radial peripheral groove 24. The ball thrust pieces present in the housing 34 act with the annular projections 30 of the actuating rod 4 as additional means for securing against loss.

As already mentioned in connection with FIG. 4, the hollow tube 28 on its housing 34 may be retracted against the force of the spring elements 32 to such an extent that an unhindered latching to the implant is made possible. The latching of the manipulating tool 2 to the implant takes place subsequently by the action of the spring force of the spring elements 32 as soon as the projections 36 are located in the appropriate position for engagement in corresponding counter elements of the implant. Thus the rotational securing of the implant relative to the manipulating tool 2 takes place automatically after axial fixing has taken place by means of the clamping jaws 10 and may therefore not be overlooked.

Figure 7:
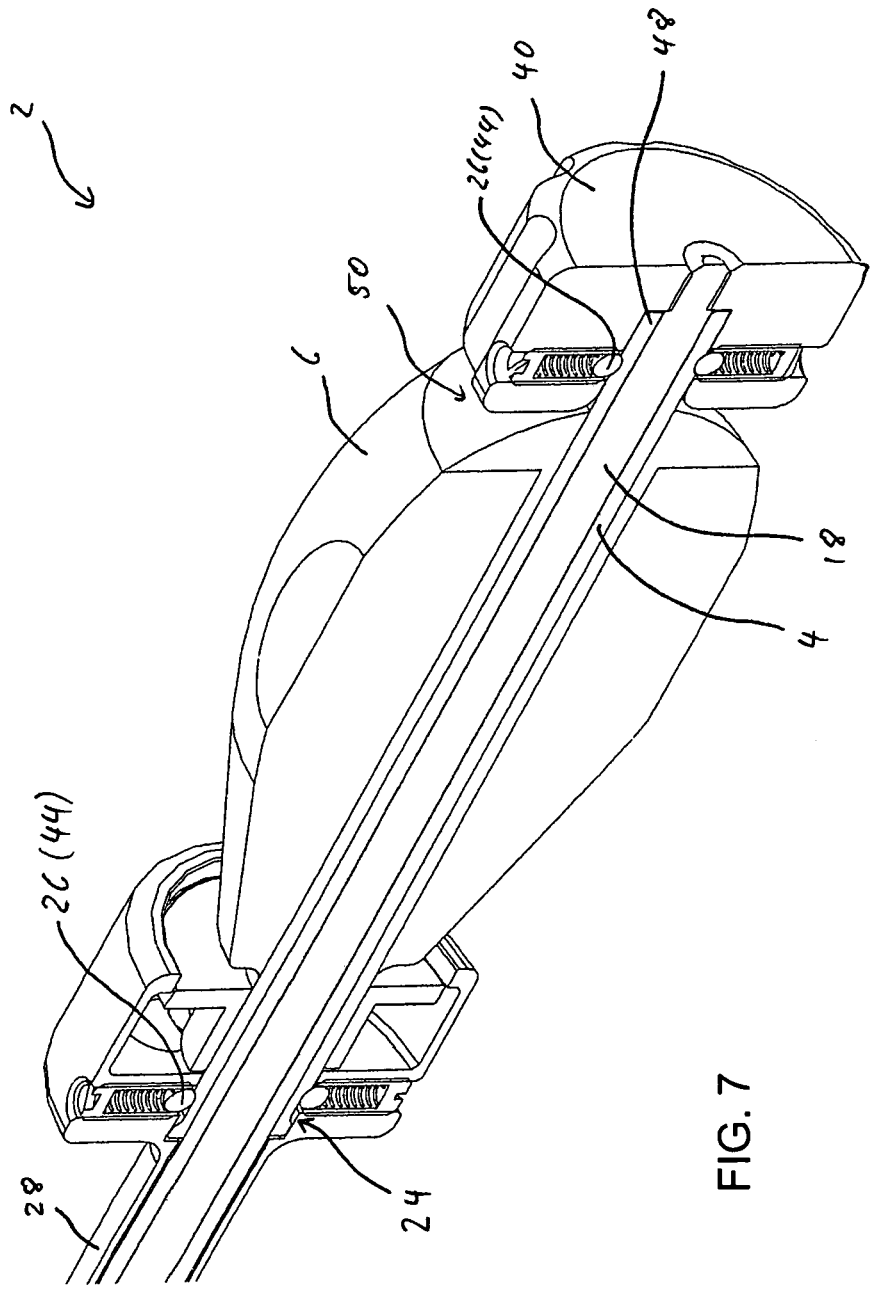
FIG. 7 shows a perspective longitudinal section through a manipulating tool in the region of its rear end.

FIG. 7 shows the rear end of the manipulating tool 2. The latching element 26 of the hollow tube 28 in the form of a ball 44 engaging in the peripheral groove 24, has axial clearance in the peripheral groove 24 of the actuating rod 4. This axial clearance defines the positions of the hollow tube 28 shown in FIGS. 5a and 5b. The projections 36 connected to the hollow tube 28 may thus be moved by a defined axial movement path.

The grip part 6 of the actuating rod 4 has at its rear end a further radial peripheral groove, into which a further latching element 26 engages with a positive connection effective in the axial direction. The latching element 26 is incorporated in the rotary grip 40, and may in turn be in the shape of a ball 44 of a ball thrust piece. The grip part 6 is at its rear end extended by an extension 48 which bears the radial peripheral groove (not denoted further).

As already mentioned in connection with FIG. 4, the drive shaft 18 and/or the drive pinion 38 connected thereto has a neutral position and an operating position. In the neutral position, as shown in FIG. 7, the drive shaft 18 is fixed releasably by an axially effective positive connection. This fixing serves at the same time for securing the drive shaft 18 against loss relative to the actuating shaft 4 and/or the grip part 6. In an engagement position, the drive shaft 18 on the rotary knob 40 is pushed forward in the axial direction of the actuating rod 4. For clearly defining the engagement position of the drive pinion 38, the grip part 6 at its rear end comprises a bearing surface 50 which cooperates with a corresponding opposing bearing surface of the rotary knob 40. The engagement position is defined by the contact of the bearing surfaces 50, but no latching which is effective in the axial direction is produced. The lack of this latching has the effect that the drive shaft 18 may be very easily pulled back from the engagement position into the more stable neutral position.

Figure 8:
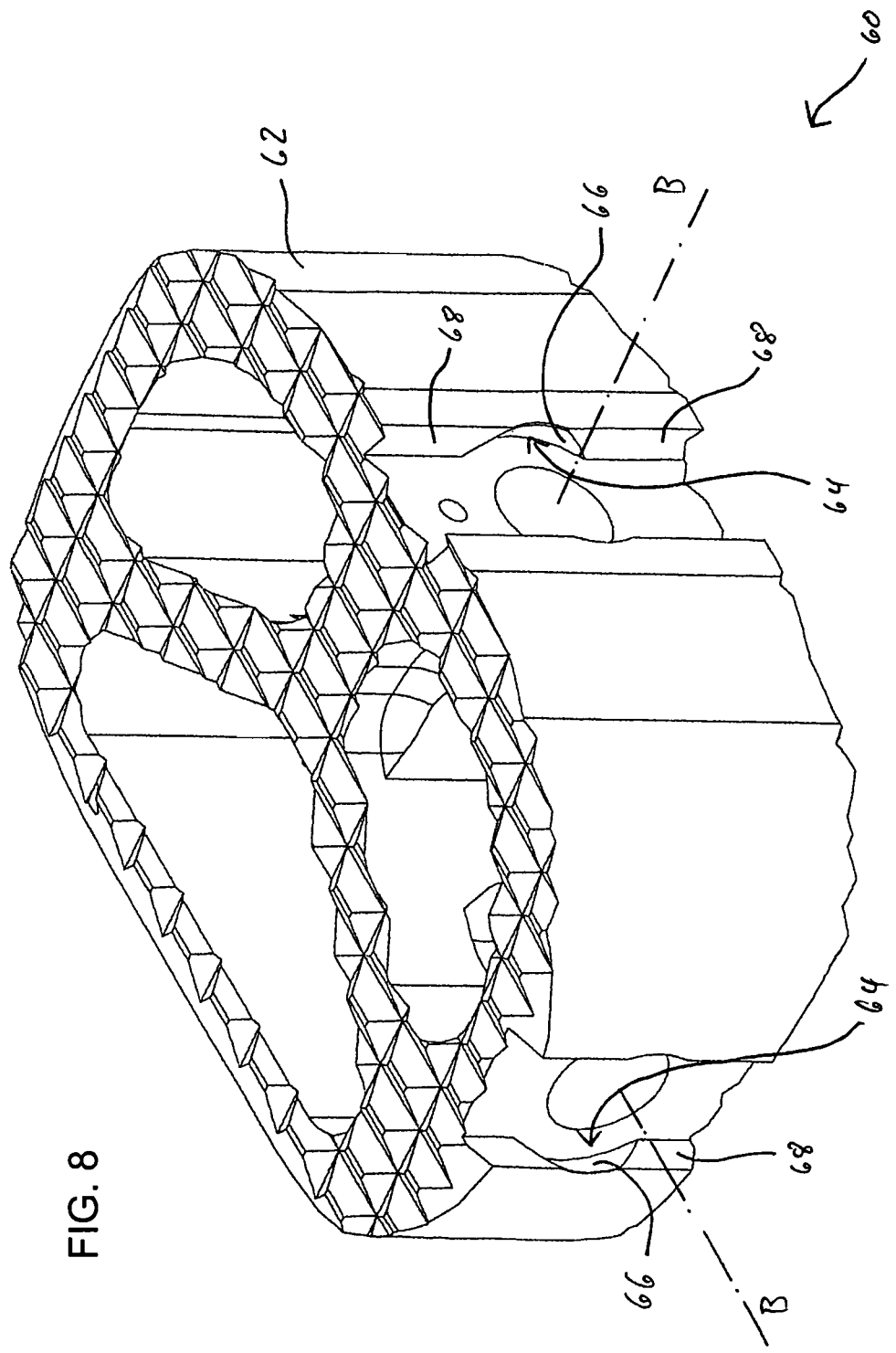
FIG. 8 shows an implant in perspective view and FIGS. 9 and 10 show an implant as well as the front end of an associated manipulating tool in perspective view and/or in cross section.

FIG. 8 shows an implant 60 according to one embodiment. The implant 60 has a body 62 on which a counter element is present for releasably fixing a manipulating tool 2, in particular the manipulating tool 2 described above. The body 62 of the implant 60 has two axes B. A manipulating tool is coaxially connected to the implant 60 at these axes B.

For the non-positive connection of the implant 60 to a manipulating tool 2 the implant 60 has a counter element with at least two undercuts 64 spaced apart relative to its axes B. Each undercut 64 has a holding surface 66 oriented in the direction of the interior of the body 62.

For handling the implant 60 shown in FIG. 8 with the manipulating tool 2, said manipulating tool engages with the clamping jaws 10 in the undercuts 64. From now on, a non-positive connection is present between the surfaces 14 of the clamping jaws 10 and the holding surfaces 66 of the undercuts 64 oriented in the direction of the interior of the body 62.

The undercuts 64 are incorporated in the wall of the body 62 of the implant 60, but for example may also be formed by strips or similarly formed bodies present on the surface of the body 62.

The implant 60 has bearing surfaces 68 which cooperate with the fixing surfaces 42 (see FIG. 5b) of the projection 36 of the hollow tube 28. The implant 60 may be connected fixedly in terms of rotation to the manipulating tool 2 in this manner. The bearing surfaces 68 are oriented parallel to the respective axis B which substantially simplifies the insertion of the manipulating tool 2.

Figure 9:
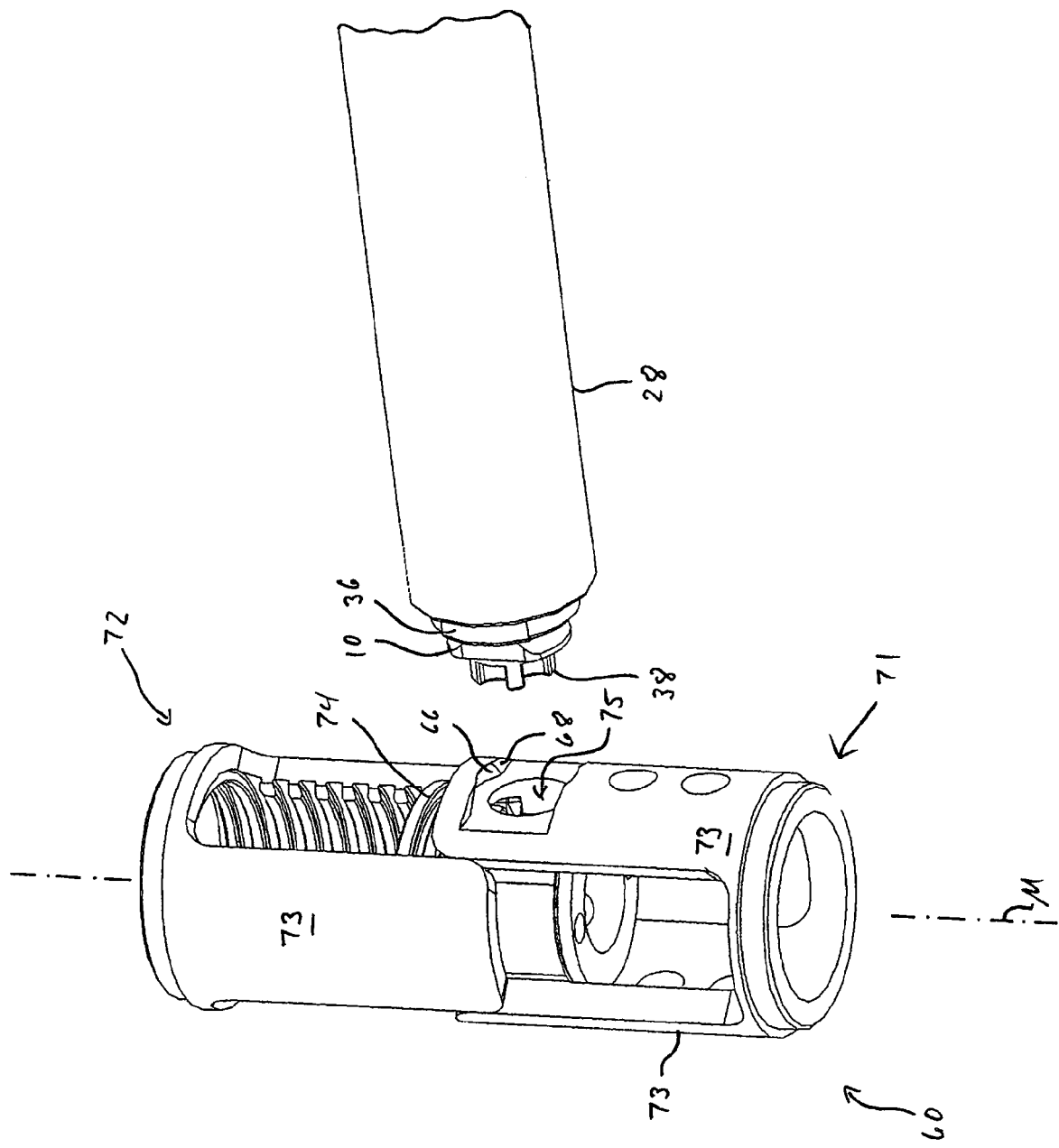

FIG. 9 shows a further embodiment for an implant 60 together with the front part of a manipulating tool 2. The implant 60 and the manipulating tool 2 form an advantageously cooperating kit of parts.

The implant 60 shown in FIG. 9, has a first and a second component 71, 72 which form the body 62 of the implant 60. The first and second components 71, 72 are axially movable along a central longitudinal axis M of the implant 60 and held against one another fixedly in terms of rotation. The two components 71, 72 respectively have at least two wall segments 73 fixed to a base. The wall segments 73 extend respectively at a radial distance from one another both in the direction of the central longitudinal axis M and in the peripheral direction of the implant 60. Wall segments 73 adjacent to one another flank in the peripheral direction an intermediate space in which one wall segment 73 of the other component 71, 72 respectively extends and is axially guided therein.

The two components 71, 72 are displaceable relative to one another so that the height and/or length of the implant 60 may be adjusted. For adjusting the length and/or height of the implant 60 a drive element 74 present in the interior cooperates with the second component 72 in the manner of a screw mechanism. To this end, the drive element 74 has an external thread which meshes with an internal thread present on the inside of the wall segments 73 of the second component 72. By rotating the drive element 74 about the central longitudinal axis M of the implant 60, the second component 72 may be moved relative to the first component 71. For actuating the drive element 74, in one wall segment 73 an access opening 75 is located through which the drive pinion 38 of the manipulating tool 2 may access the drive element 74.

The drive element 74 has on its underside a crown wheel accessible for the drive pinion 38 (which is moved through the access opening 75 into the interior of the implant 60). The crown wheel of the drive element 74 and the drive pinion 38 cooperate in the manner of a crown wheel gear. The drive element 74 is supported relative to the first component 71 in the loading direction i.e. along the central longitudinal axis M of the implant 60.

In order to allow a positioning of the implant 60, the manipulating tool 2 is connected to the implant 60 fixedly in terms of rotation via the clamping jaws 10 in the axial direction and to the projections 36.

Figure 10:
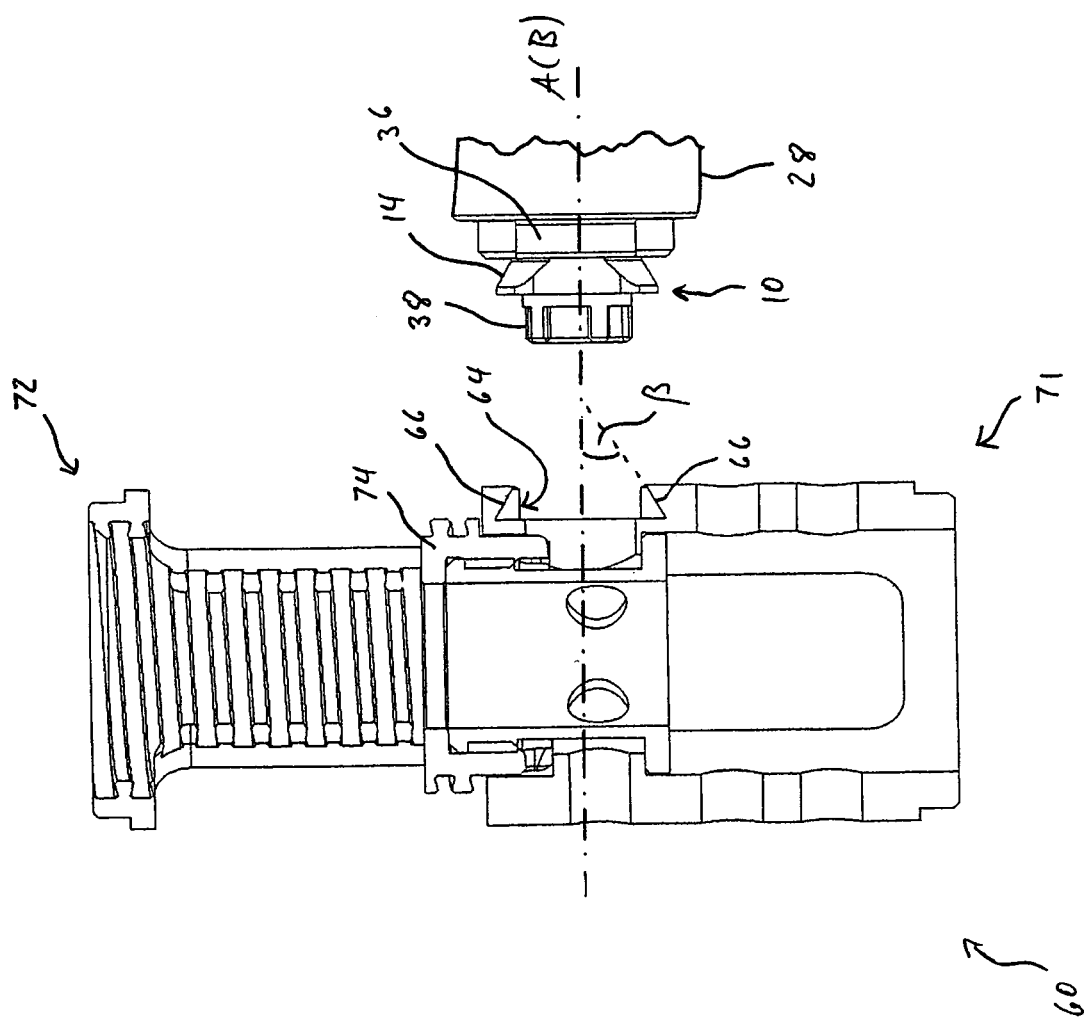

FIG. 10 shows a cross section through the implant 60 known from FIG. 9, and the front part of the manipulating tool 2 in a plane which contains the central longitudinal axis A and an axis B of the implant 60. The manipulating tool 2 is connected to the implant 60 such that the central longitudinal axis A coincides with the axis B of the implant 60.

The holding surfaces 66 enclose with the axis B an acute angle β open toward the interior of the implant 60. In particular, the angle β may correspond to the abovementioned angle α, which the clamping jaws 10 enclose with the central longitudinal axis A in the direction of the front part of the manipulating tool 2. For improving the non-positive connection between the holding surfaces 66 of the implant 60 and the surfaces 14 of the clamping jaws 10 of the manipulating tool 2, the holding surfaces 66 form part of a conical surface widening toward the interior of the implant 60.

The implant 60 has bearing surfaces 68 which are not oriented coaxially to the axis B (see also FIGS. 8 and 9). Preferably the bearing surfaces 68 are oriented parallel to the axis B. The bearing surfaces 68 cooperate with the fixing surfaces 42 of the manipulating tool 2 (see FIG. 5b) and allow the rotational fixing of the implant 60 relative to the manipulating tool 2.

The connection between the manipulating tool 2 and the implant 60 is produced initially by the actuating rod 4 and/or the clamping jaws 10 being rotated by 90° relative to the position shown in FIGS. 9 and 10 about the central longitudinal axis A. The clamping jaws 10 are subsequently moved in the region of the flattened portion present on the outside of the implant 60. In this case, the manipulating tool 2 is guided such that its central longitudinal axis A and the axis B of the implant 60 coincide. Subsequently, the manipulating tool 2 is rotated by 90° about its central longitudinal axis A, so that the clamping jaws 10 engage in the undercuts 64. In this connection, the surfaces 14 of the clamping jaws 10 and the holding surfaces 66 of the implant 60 are brought to bear positively against one another.

The implant 60 and the manipulating tool 2 are now axially connected to one another i.e. along the central longitudinal axis A of the manipulating tool 2 and/or along the axis B of the implant 60. A rotational fixing of the implant 60 is already possible at this time by a possibly present frictional connection between the surface 14 of the clamping jaws 10 and the holding surface 66 of the implant 60.

By engaging the projections 36 on the bearing surfaces 68, the implant 60 may now be locked relative to the manipulating tool 2 fixedly in terms of rotation. For the height adjustment of the implant 60, the drive pinion 38 may be subsequently pushed along the central longitudinal axis A of the manipulating tool 2 sufficiently far forward that said manipulating tool reaches its position of engagement and meshes with the crown wheel present on the underside of the drive element 74 for driving the drive element.

The invention claimed is:

1. A manipulating tool for a medical implant, comprising:
an actuating rod defining a central longitudinal axis and having a front end and a rear end;
a grip part fixed on said rear end of said actuating rod;
a fixing element at said front end of said actuating rod, for releasably axially fixing the implant, said fixing element having at least two clamping jaws spaced at a radial distance from said central longitudinal axis of said actuating rod and, relative to an imaginary cylinder surface extending coaxially with said central longitudinal axis, mutually spaced apart in a peripheral direction, for respectively engaging behind at least one counter element on the implant;
a locking device for rotationally locking the manipulating tool to the implant, said locking device including at least one locking element held in a rotationally fixed connection with said actuating rod and held axially displaceably on said actuating rod between a front position, defining an operating position thereof, and a rear position, defining a position of repose thereof, and said at least one locking element being configured for engaging with a stop surface of the implant in a rotationally fixed manner, said locking device including a hollow tube enclosing said actuating rod and being axially displaceable thereon, said hollow tube having a front end carrying said at least one locking element fixedly connected thereto; and
said clamping jaws having outer edges facing away from said central longitudinal axis and disposed at a common radial distance from a circle circumscribing said clamping jaws, said common radial distance being constant irrespective of said locking element being in the operating position or the position of repose.

2. The manipulating tool according to claim 1, wherein said at least one locking element is spring-loaded in a direction of the operating position thereof.

3. The manipulating tool according to claim 1, which comprises at least one spring element having a rear end supported on said actuating rod and a front end supported on said hollow tube.

4. A manipulating tool for a medical implant, comprising:
an actuating rod defining a central longitudinal axis and having a front end and a rear end;
a grip part fixed on said rear end of said actuating rod;
a fixing element at said front end of said actuating rod, for releasably axially fixing the implant, said fixing element having at least two clamping jaws spaced at a radial distance from said central longitudinal axis of said actuating rod and, relative to an imaginary cylinder surface extending coaxially with said central longitudinal axis, mutually spaced apart in a peripheral direction, for respectively engaging behind at least one counter element on the implant;
a locking device for rotationally locking the manipulating tool to the implant, said locking device including at least one locking element held in a rotationally fixed connection with said actuating rod and held axially displaceably on said actuating rod between a front position, defining an operating position thereof, and a rear position, defining a position of repose thereof, and said at least one locking element being configured for engaging with a stop surface of the implant in a rotationally fixed manner, said locking device including a hollow tube enclosing said actuating rod and being axially displaceable thereon, said hollow tube having a front end carrying said at least one locking element fixedly connected thereto; and said clamping jaws having outer edges facing away from said central longitudinal axis and disposed at a common radial distance from a circle circumscribing said clamping jaws, said common radial distance being constant irrespective of said locking element being in the operating position or the position of repose;

at least one spring element having a rear end supported on said actuating rod and a front end supported on said hollow tube, said rear end of said hollow tube being radially widened, forming a housing, and said at least one spring element being disposed in said housing.

5. The manipulating tool according to claim 1, wherein said hollow tube is mounted to be secure against loss on the actuating rod.

6. The manipulating tool according to claim 5, which comprises a latching element securing said hollow tube against loss, said latching element is spring-loaded substantially in the radial direction, engages in a peripheral groove with axial clearance, the axial clearance corresponding to a movement path between the operating position and the position of repose.

7. The manipulating tool according to claim 6, which comprises at least one protruding annular projection on an outer periphery of said actuating rod, between said front end and said peripheral groove.

8. The manipulating tool according to claim 1, wherein said hollow tube is rotationally fixed by a flattened portion on said actuating rod and a projection, said flattened portion on said actuating rod extending axially at least over a front partial region and reaching into a front face thereof, and said projection is disposed on an inner face of said hollow tube, and bears with a flat side against said flattened portion.

9. The manipulating tool according to claim 8, wherein said flattened portion is formed by a base of an axial groove, and said projection is formed to extend therein with a complementary configuration.

10. The manipulating tool according to claim 9, wherein said projection projects beyond a front face at said front end of said hollow tube and forms said at least one locking element.

11. The manipulating tool according to claim 1, wherein said outer edges of said clamping jaws describe segments of a common circular arc.

12. The manipulating tool according to claim 1, wherein said clamping jaws are formed with surfaces on sides thereof, said surfaces for cooperating with the counter element, said surfaces facing rearwardly towards said rear end, enclosing said central longitudinal axis of said actuating rod, and extending along an angle opening toward the front end thereof.

13. The manipulating tool according to claim 12, wherein said surfaces are conical surfaces tapering toward said rear end.

14. The manipulating tool according to claim 1, wherein said actuating rod and said grip part are penetrated by a central bore, and wherein a drive shaft is received in said central bore, said drive shaft having a front end with a drive pinion and a rear end with a rotary knob.

15. The manipulating tool according to claim 14, wherein said drive shaft is axially displaceable between a neutral position and an engagement position, wherein a front face of said drive pinion is located axially to the rear in the neutral position and is located axially in front of a front face of said actuating rod in the engagement position.

16. The manipulating tool according to claim 14, wherein said grip part has a rear end formed with a radial peripheral groove, and wherein a spring-loaded latching element present in said rotary knob is disposed to engage in said groove with a positive connection effective in the axial direction.

17. The manipulating tool according to claim 15, wherein the engagement position is defined by a bearing surface formed on said grip part and cooperating with said rotary knob.

18. A kit of parts, comprising:
a medical implant, including:
a body defining an axis and having an interior;
a counter element disposed on said body, said counter element having at least two undercuts spaced apart relative to said axis of said body and each having a respective holding surface oriented towards the interior of the body; and
a bearing surface on said counter element oriented non-coaxially with said axis of said body;
a manipulating tool for manipulating said medical implant, said manipulating tool including:
an actuating rod defining a central longitudinal axis and having a front end and a rear end;
a grip part fixed on said rear end of said actuating rod;
a fixing element at said front end of said actuating rod, for releasably axially fixing said manipulating tool to said body of said medical implant, said fixing element having at least two clamping jaws spaced at a radial distance from said central longitudinal axis of said actuating rod and, relative to an imaginary cylinder surface extending coaxially with said central longitudinal axis, mutually spaced apart in a peripheral direction, for respectively engaging behind said holding surfaces formed on said counter element;
a locking device for rotationally locking said manipulating tool to said implant, said locking device including at least one locking element held in a rotationally fixed connection with said actuating rod and held axially displaceably on said actuating rod between a front position, wherein said locking element engages with said bearing surface on said counter element, and a rear position, defining a position of repose thereof, and said locking element being configured for engaging with said bearing surface in a rotationally fixed manner, said locking device including a hollow tube enclosing said actuating rod and being axially displaceable thereon, said hollow tube having a front end carrying at least one locking element fixedly connected thereto; and
said clamping jaws having outer edges facing away from said central longitudinal axis and disposed at a common radial distance from a circle circumscribing said clamping jaws, said common radial distance being constant irrespective of said locking element being in the operating position or the position of repose.

* * * * *